United States Patent
Xiao

(10) Patent No.: US 9,162,956 B2
(45) Date of Patent: Oct. 20, 2015

(54) PROCESS AND DEVICE FOR PREPARING CYCLOHEXANOL AND CYCLOHEXANONE BY CYCLOHEXANE OXIDATION

(76) Inventor: Zaosheng Xiao, Suzhou (CN)

( * ) Notice: Subject to any disclaimer, the term of this patent is extended or adjusted under 35 U.S.C. 154(b) by 0 days.

(21) Appl. No.: 14/384,203

(22) PCT Filed: May 17, 2012

(86) PCT No.: PCT/CN2012/075642
§ 371 (c)(1),
(2), (4) Date: Sep. 10, 2014

(87) PCT Pub. No.: WO2013/143212
PCT Pub. Date: Oct. 3, 2013

(65) Prior Publication Data
US 2015/0105590 A1    Apr. 16, 2015

(30) Foreign Application Priority Data
Mar. 28, 2012 (CN) .......................... 2012 1 0084939

(51) Int. Cl.
| C07C 45/53 | (2006.01) |
| B01J 8/00 | (2006.01) |
| C07C 29/132 | (2006.01) |
| C07C 407/00 | (2006.01) |
| B01J 19/00 | (2006.01) |
| B01J 19/24 | (2006.01) |

(52) U.S. Cl.
CPC .............. *C07C 45/53* (2013.01); *B01J 8/0015* (2013.01); *B01J 19/006* (2013.01); *B01J 19/24* (2013.01); *C07C 29/132* (2013.01); *C07C 407/00* (2013.01); *B01J 2208/00752* (2013.01); *B01J 2219/0011* (2013.01); *B01J 2219/00081* (2013.01); *B01J 2219/00101* (2013.01); *B01J 2219/00768* (2013.01); *B01J 2219/182* (2013.01); *C07C 2101/14* (2013.01)

(58) Field of Classification Search
CPC ................................. C07C 45/53; C07C 29/50
USPC ........................... 568/354, 357, 836; 422/187
See application file for complete search history.

(56) References Cited

U.S. PATENT DOCUMENTS

| 3,927,105 A | 12/1975 | Brunie et al. |
| 2004/0158103 A1 | 8/2004 | Pirutko et al. |

FOREIGN PATENT DOCUMENTS

| CN | 1147499 | 4/1997 |
| CN | 1621398 | 6/2005 |
| CN | 202170313 | 3/2012 |

*Primary Examiner* — Sikarl Witherspoon

(57) ABSTRACT

A process for preparing cyclohexanol and cyclohexanone by cyclohexane oxidation includes steps of: non-catalyticly oxidizing cyclohexane with molecular oxygen in the air to obtain an oxidation mixture containing CHHP as a main product; performing a homogenous catalytic decomposition of the CHHP to obtain cyclohexanol and cyclohexanone; and rectifying to obtain products of the cyclohexanol and the cyclohexanone, wherein the step of performing the homogenous catalytic decomposition involves a homogeneous catalytic decomposition reaction and distillation vessel which removes water via azeotropic rectification to reduce a water content of a decomposition liquid to be below 100 ppm. A device therefor includes the homogeneous catalytic decomposition reaction and distillation vessel for performing the homogenous catalytic decomposition of the CHHP. The homogeneous catalytic decomposition reaction and distillation vessel and pipelines thereof are free from scale formation, which elongates a production cycle to be over one year.

12 Claims, 2 Drawing Sheets

PROCESS AND DEVICE FOR PREPARING CYCLOHEXANOL AND CYCLOHEXANONE BY CYCLOHEXANE OXIDATION

CROSS REFERENCE OF RELATED APPLICATION

This is a U.S. National Stage under 35 U.S.C. 371 of the International Application PCT/CN2012/075642, filed May 17, 2012, which claims priority under 35 U.S.C. 119(a-d) to CN 201210084939.1, filed Mar. 28, 2012.

BACKGROUND OF THE PRESENT INVENTION

1. Field of Invention

The present invention relates to a process and a device for preparing cyclohexanol and cyclohexanone by cyclohexane oxidation.

2. Description of Related Arts

The conventional process for the preparation of cyclohexanol and cyclohexanone comprises: non-catalyticly oxidizing cyclohexane with molecular oxygen to obtain an oxidation mixture containing cyclohexyl hydroperoxide (CHHP) as a main product; decomposing the CHHP to obtain cyclohexanol and cyclohexanone; and rectifying to obtain products of the cyclohexanol and the cyclohexanone. Internationally, the art of catalyticly decomposing the CHHP to obtain the cyclohexanol and the cyclohexanone comprises two manners: the homogeneous catalytic decomposition by bis(tert-butyl) chromate, disclosed by French Rhodia Company; and, the heterogeneous catalytic decomposition by cobalt acetate in the alkaline aqueous solution of sodium hydroxide, disclosed by Dutch DSM.

The homogeneous catalytic decomposition of CHHP by the bis(tert-butyl) chromate has two serious defects. Firstly, during decomposing, the scale formation, mainly the chromium adipate, blocks equipments and pipelines. Disclosed by Rhodia, the phosphoric acid octyl ester is used as the scale inhibitor, which still fails to completely solve the scale formation. The continuous production cycle only lasts for four months; washing and descaling after stalling the production device are executed three times per year. Secondly, the conversion rate is low, wherein the molar conversion rate is only around 92%; and around 5% of the CHHP still remains in the decomposed materials. The remaining CHHP is decomposed under the conditions of a high concentration of cyclohexanol and cyclohexanone, high acidity and a high temperature inside the cyclohexane recycling columns and the cyclohexanol and cyclohexanone product columns, so as to mainly produce acid compounds, like adipic acid, and ester compounds, mainly caprolactone; to speed up the condensation reaction of free radicals of the cyclohexanol and the cyclohexanone, and the esterification reaction of cyclohexanol; and to generate the high-boiling-point substances and reduce the yield. Conventionally, a total molar yield of the worldwide industrial devices adopting the art of the homogeneous catalytic decomposition of CHHP by the bis(tert-butyl) chromate is only around 80%.

The heterogeneous catalytic decomposition by cobalt acetate in the alkaline aqueous solution of sodium hydroxide also has two defects. Firstly, the alkaline decomposition normally compromises with the big secondary reactions, and induces a low decomposition molar yield of only 84%. Secondly, it is difficult to completely separate the cyclohexane oil phase containing cyclohexanol and cyclohexanone from the alkaline aqueous phase containing the alkaline waste. The oil phase always contains a certain amount of the waste alkaline aqueous phase, in such a manner that the scales of the waste alkaline are always formed in the rectification towers subsequently, which blocks the rectification columns and the reboilers thereof, and results in the continuous production cycle of only six months. Conventionally, a total molar yield of the worldwide industrial devices adopting the art of the heterogeneous catalytic decomposition by cobalt acetate in the alkaline aqueous solution of sodium hydroxide is only around 80%.

Conventionally, the worldwide companies respectively adopt one of the above two manners to accomplish decomposing the CHHP at one step. The Chinese patents ZL9411039.9 and ZL98112730.4, filed by the inventor of this application, disclose the two-step alkaline decomposition art. At the first step thereof, the alkalinity is lowered; the recycling amount of the alkaline aqueous phase is increased; the static mixer and the plug flow tower-typed decomposing reactor are used. Industrial application results indicate that, the total molar yield of the device thereof really increases, but the separation of the cyclohexane oil phase from the waste alkaline aqueous phase becomes more difficult. The several sets of industrial production devices of the whole two-step alkaline decomposition art have a molar total yield of around 82%.

SUMMARY OF THE PRESENT INVENTION

An object of the present invention is to provide a process and a device for preparing cyclohexanol and cyclohexanone by cyclohexane oxidation at a fast reaction speed, with a relatively high total yield and in a relatively long continuous production cycle.

Accordingly, in order to accomplish the above objects, the present invention provides a process for preparing cyclohexanol and cyclohexanone by cyclohexane oxidation, which comprises steps of: non-catalyticly oxidizing cyclohexane with molecular oxygen in the air to obtain an oxidation mixture containing cyclohexyl hydroperoxide (CHHP) as a main product; performing a homogenous catalytic decomposition of the CHHP to obtain cyclohexanol and cyclohexanone; and rectifying to obtain products of the cyclohexanol and the cyclohexanone, wherein the step of performing the homogenous catalytic decomposition of the CHHP involves a homogeneous catalytic decomposition reaction and distillation vessel which removes water via azeotropic rectification to reduce a water content of a decomposition liquid to be below 100 ppm.

Preferably, the homogeneous catalytic decomposition reaction and distillation vessel comprises a decomposition reaction and distillation vessel having 3~5 decomposition reaction chambers. A tubular heater bundle with steam serving as a heating medium is provided in the decomposition reaction and distillation vessel; a dehydration and rectification column is connected to the decomposition reaction and distillation vessel. The step of performing the homogenous catalytic decomposition of the CHHP comprises steps of:

heating a decomposition reaction liquid by the tubular heater bundle to evaporate cyclohexane in the decomposition reaction liquid;

controlling a flow of the steam as the heating medium to evaporate 20~40 wt % of the cyclohexane in the decomposition reaction liquid in the decomposition reaction and distillation vessel;

entering, by the evaporated cyclohexane, the dehydration and rectification column to be further dehydrated and purified, and then entering, by the evaporated cyclohexane, a condenser at a top of the dehydration and rectification column to be cooled;

next, refluxing a part of the cyclohexane in a liquid phase at a reflux ratio of 0.3~0.5, and returning the rest cyclohexane to an oxidation reactor after rinsing with water, wherein a content of the cyclohexanol and the cyclohexanone in the part of the cyclohexane is lower than 0.04% by controlling the reflux;

to a first chamber of the decomposition reaction and distillation vessel continuously adding an oil-soluble transitional metal catalyst whose amount is determined to ensure that a content of transitional metal ions in cyclohexane oxidation liquid is 12±10 ppm; and to a second chamber of the decomposition reaction and distillation vessel continuously adding oil-soluble 1-hydroxy ethidene-1,1-diphosphonic acid (di)octyl ester which serves as a scale inhibitor, wherein a weight ratio of the added scale inhibitor and the transitional metal ions of the catalyst is 1:0.8~1.2. During performing the homogenous catalytic decomposition of the CHHP, a decomposition temperature is controlled at 80° C.~160° C., and a pressure is controlled at 0~1 MPa, wherein the pressure is a gauge pressure.

Preferably, the oil-soluble transitional metal catalyst is one member selected from a group consisting of bis(tert-butyl) chromate, cobalt naphthenate and cobalt octoate; the amount of the catalyst is determined to ensure that the content of the transitional metal ions in the cyclohexane oxidation liquid is 12±8 ppm.

Preferably, during performing the homogenous catalytic decomposition of the CHHP, the decomposition temperature is controlled at 90±2° C., and the pressure is controlled at 0.03±0.01 MPa, wherein the pressure is the gauge pressure.

Preferably, during performing the homogenous catalytic decomposition of the CHHP, the weight ratio of the added oil-soluble 1-hydroxy ethidene-1,1-diphosphonic acid (di) octyl ester and the transitional metal ions of the catalyst is 1:1.

Preferably, a reactor residence time of an oxidation mixture liquid containing CHHP in each decomposition reaction chamber of the decomposition reaction and distillation vessel is at a range of 5~8 minutes, totaling 20~40 minutes.

Preferably, during performing the homogenous catalytic decomposition of the CHHP, the flow of the steam as the heating medium is controlled to evaporate 30±5% of the cyclohexane in the reaction and distillation vessel.

The present invention also provides a homogeneous catalytic decomposition reaction and distillation vessel which is a decomposition reaction and distillation vessel having 3~5 decomposition reaction chambers provided therein. A tubular heater bundle which usually has steam serving as a heating medium is provided in each decomposition reaction chamber; a separating board with a through hole is provided between each two decomposition reaction chambers.

According to the present invention, a first part of cyclohexane is heated by the steam to be vaporized, and a second part of the cyclohexane is vaporized by reaction heat of the decomposition reaction of CHHP. The vaporized cyclohexane is so intensely stirred that each reaction chamber becomes a full backmixing decomposition reaction chamber, in such a manner that a molar conversion rate of the homogeneous catalytic decomposition of the CHHP reaches 90±5%, and a molar yield of cyclohexanone and cyclohexanol generated thereby reaches ≥94%.

According to the present invention, because of the strong water-removal via the azeotropic rectification and the steam heating of the tubular heater bundles, the following decomposition reaction speeds up:

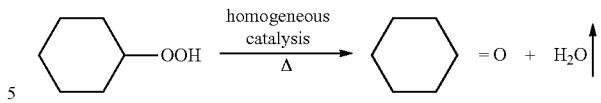

Researches indicate that, in the CHHP decomposition art of the French Rhodia, a decomposition reactor has a stirrer for stirring, but no heating and rectifying tubes; a decomposition reaction releases reaction heat which is only enough to evaporate a small amount of the cyclohexane and unable to completely remove water within reactants and water generated by chemical reactions; oxidation and decomposition liquid containing CHHP compromises with oxidation byproducts, comprising thousands ppm of adipic acid and low carbonate which belong to organic acids with a low molecular weight and thus have a strong hydrophilic property, so as to form hydronium ions and lower volatility of water molecules. In the meantime, the transitional metal ions of the homogeneous catalyst and the adipic acid generate salts which are liable to adsorb moisture and more liable to form hydronium ions with the water molecules, which further weaken the volatility of the water molecules. Without an evaporation of a large amount of cyclohexane and a water removal via the azeotropic rectification, the water aggregates with the adipic acid, the low carbonate and the transitional metal ions of the catalyst, so as to form a third phase un-soluble with the cyclohexane phase. In other words, in the CHHP decomposition art of the French Rhodia, the decomposition reactor has a gas phase main containing cyclohexane, a non-polar oil phase mainly containing cyclohexane, and a polar viscous third phase mainly containing the water, the adipic acid, the low carbonate and the transitional metal ions of the catalyst. A formation of the third phase reduces a catalytic activity of the homogenous catalyst; the third phase is liable to precipitate at a bottom of the decomposition reactor and attach to walls of equipments and pipelines. The acidic materials dissolved in the third phase slowly react and polymerize with the metal ions; once the water finally volatilizes, scale formation emerges and blocks up the equipments and the pipelines.

According to the present invention, during the homogeneous catalytic decomposition and rectification, the steam for heating accelerates the vaporizing and evaporating in the decomposition reaction and distillation vessel of the cyclohexane in the cyclohexane oxidation mixture liquid. Accordingly, a large amount of gaseous cyclohexane is generated and intensely stirs materials within the decomposition reaction and distillation vessel; water generated by the decomposition reaction readily undergoes the azeotropic rectification, so as to prevent generation of a third phase and prevent precipitation and scale formation of the homogeneous catalyst. As a result, an activity of the homogeneous catalyst is enhanced, and a ratio of cyclohexanone and cyclohexanol is increased. The added scale inhibitor further ensures that the homogeneous catalytic decomposition and distillation vessel and correspondent pipelines no longer suffer from the scale formation, which elongates a production cycle to be more than one year.

These and other objectives, features, and advantages of the present invention will become apparent from the following detailed description, the accompanying drawings, and the appended claims.

BRIEF DESCRIPTION OF THE DRAWINGS

In FIG. 1: 1—cyclohexane oxidation device; 2—pipeline I; 3—heat exchanger; 4—pipeline II; 5—dehydration and rectification column; 6—condenser; 7—separator for separating cyclohexane and acidic water; 8—decomposition reaction and distillation vessel; 9—pipeline III; 10—pipeline IV; 11—pipeline V; 12—pipeline VI; 13—discharging pump; 14—secondary in-depth decomposition reaction system; 15—pipeline VII; 16—pipeline VIII; 17—pipeline IX; 18—pipeline X; 19—pipeline XI; 20—pipeline XII.

DETAILED DESCRIPTION OF THE PREFERRED EMBODIMENT

Combined with the preferred embodiments, the present invention is further illustrated.

Figure 1:
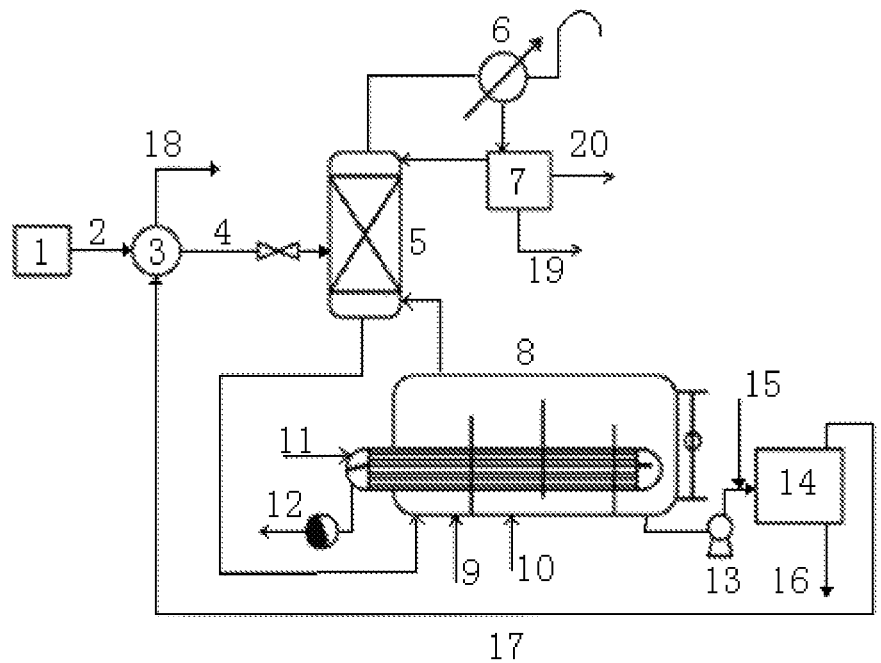
FIG. 1 is a sketch view of a device and a process for preparing cyclohexanol and cyclohexanone by cyclohexane oxidation according to a preferred embodiment of the present invention.

Referring to FIG. 1 of the drawings, according to a preferred embodiment of the present invention, in a cyclohexane oxidation device 1, cyclohexane is non-catalytically oxidized with molecular oxygen in the air to generate an oxidation mixture 381,788 Kg/h containing CHHP as a main product at 166° C., wherein the oxidation mixture comprises (wt %):
  CHHP: 3.4%;
  Cyclohexanol: 0.37%;
  Cyclohexanone: 0.26%;
  Acid: 0.28%;
  Ester: 0.28%; and
  Other light components and heavy components: 0.14%.

The oxidation mixture at 166° C. exchanges heat with a decomposition liquid in a heat exchanger 3 through a pipeline I 2, so as to generate an oxidation mixture liquid at 114° C. The oxidation mixture liquid enters a dehydration and rectification column 5 or a first chamber of a decomposition reaction and distillation vessel 8 through a pipeline II for flash evaporation and dehydration. Chromic acid tert-butyl ester containing 3 wt % of chromium is added at a rate of 100 Kg·h as a catalyst into the first chamber of the decomposition reaction and distillation vessel 8 through a pipeline III 9. A tubular heater bundle in the decomposition reaction and distillation vessel 8 is inputted with steam which serves as a heating medium through a pipeline V 11, and resulting condensate water is discharged through a pipeline VI 12. Because of a strong exothermic property of a CHHP decomposition reaction and the heating by the tubular heater bundle, a large amount of the cyclohexane in the cyclohexane oxidation mixture liquid is evaporated in the decomposition reaction and distillation vessel 8, which intensely stirs up the reaction mixture and removes water which is generated by the CHHP decomposition via a azeotropic evaporation. A gas phase of the cyclohexane is rectified in the dehydration and rectification column 5, and condensed in a condenser 6 at a top of the dehydration and rectification column 5, so as to obtain 130,000 Kg/h of cyclohexane and water containing fewer than 0.04 wt % of cyclohexanol and cyclohexanone. Thereafter, the 130,000 Kg/h of cyclohexane and water are separated by a separator for separating cyclohexane and acidic water 7, wherein 30,000 Kg/h of the cyclohexane is refluxed at the column top; 98,764 Kg/h of the cyclohexane containing around 0.04 wt % of cyclohexanol and cyclohexanone returns to an oxidation reaction system through a pipeline XII 20; and 1236 Kg/h of the acidic water is discharged into a waste water processing device through a pipeline XI 19. A cyclohexane solution containing 10% of 1-hydroxy ethidene-1,1-diphosphonic acid (di)octyl ester is continuously added into a second chamber of the decomposition reaction and distillation vessel 8 through a pipeline IV 10 at a rate of 30 Kg/h.

The decomposition reaction and distillation vessel 8 discharges 281,918 Kg/h of a decomposition liquid into a secondary in-depth decomposition reaction system 14 through a discharging pump 13, wherein the decomposition liquid comprises (wt %):
  CHHP: 0.46%;
  Cyclohexanol: 1.61%;
  Cyclohexanone: 2.54%;
  Acid: 0.5%;
  Ester: 0.5%; and
  Other light component: 0.2%.

The decomposition reaction and distillation vessel 8 has a pressure (gauge pressure) of 0.03 MPa, and a temperature of 91° C. Via analysis, the homogeneous catalytic decomposition of the present invention has a molar conversion rate of 90% and a molar yield of 94%. Then, the homogeneous catalytic decomposition liquid is processed with an in-depth two-step heterogeneous decomposition with NaOH aqueous solution in the secondary in-depth decomposition reaction system 14, wherein fresh NaOH aqueous solution is added through a pipeline VII 15 and resulting waste alkali is discharged through a pipeline VIII 16. After the above thorough decomposition, an oil phase at 91° C. passes through the discharging pump 13, a pipeline IX 17, the heat exchanger 3 and a pipeline X 18 and then enter a rectification system. Finally, the rectification system obtains 13,190 Kg/h of 99.9% cyclohexanone products. A unit consumption of preparing the cyclohexanone by the cyclohexane oxidation is 1,000 Kg cyclohexane/ton cyclohexanone, and a total molar yield thereof is 85.71%.

Or the homogeneous catalytic decomposition liquid directly enters the rectification system, without the in-depth two-step heterogeneous decomposition with NaOH aqueous solution in the secondary in-depth decomposition reaction system 14, which finally generates 12,930 Kg/h of a mixture of cyclohexanol and cyclohexanone (KA oil, containing 98% of cyclohexanol and cyclohexanone). A unit consumption of preparing the KA oil by the cyclohexane oxidation is 1,020 Kg cyclohexane/ton KA oil, a total molar yield thereof is 81.5%.

Figure 2:
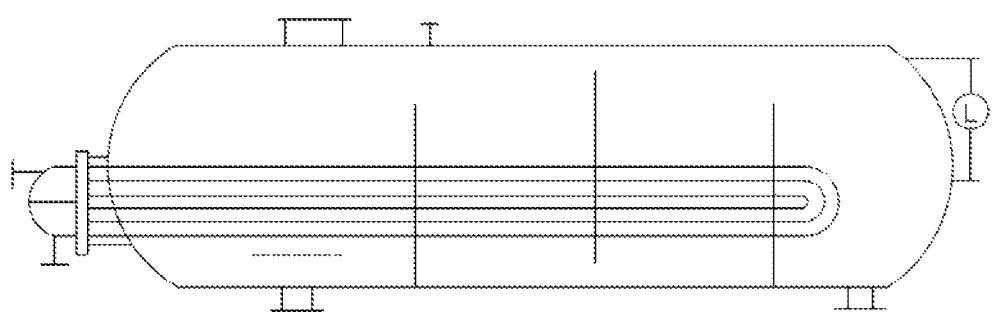
FIG. 2 is a sketch view of a decomposition reaction and distillation vessel of FIG. 1.
Figure 3:
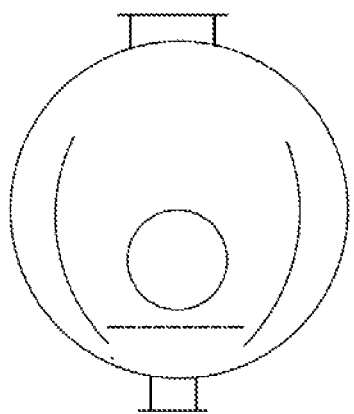
FIG. 3 is a left view of the decomposition reaction and distillation vessel of FIG. 2.

Referring to FIG. 2 and FIG. 3, according to the preferred embodiment of the present invention, the homogeneous catalytic decomposition reaction and distillation vessel 8 is a horizontal decomposition reaction and distillation vessel which has 4 decomposition reaction chambers; each decomposition reaction chamber is provided with a tubular heater bundle; a separating board with a through-hole is provided between each two decomposition reaction chamber.

According to the preferred embodiment of the present invention, because of heating by the steam during performing the homogeneous catalytic decomposition and distillation, the cyclohexane in the cyclohexane oxidation mixture liquid is accelerated to vaporize and evaporate in the decomposition reaction and distillation vessel 8; accordingly, a large amount of gaseous cyclohexane is formed and intensely stirs materials within the decomposition reaction and distillation vessel 8. Therefore, water generated by the decomposition reaction is readily removed via an azeotropic volatilization. As a result, the homogenous catalyst is prevented from precipitating and scaling; an activity of the homogeneous catalyst is enhanced, and a ratio of cyclohexanone and cyclohexanol is increased; and, the added scale inhibitor further ensures that the homogeneous catalytic decomposition and distillation vessel 8 and the correspondent pipelines no longer suffer from the scale formation, which elongates a production cycle to be more than one year.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A process for preparing cyclohexanol and cyclohexanone by cyclohexane oxidation, comprising steps of: non-catalyticly oxidizing cyclohexane with molecular oxygen in the air to obtain an oxidation mixture containing cyclohexyl hydroperoxide (CHHP) as a main product; performing a homogenous catalytic decomposition of the CHHP to obtain cyclohexanol and cyclohexanone; and rectifying to obtain products of the cyclohexanol and the cyclohexanone;

wherein the step of performing the homogenous catalytic decomposition of the CHHP comprises using a homogeneous catalytic decomposition reaction and distillation vessel which removes water via azeotropic rectification to reduce a water content of a decomposition liquid to be below 100 ppm.

2. The process, as recited in claim 1, wherein the homogeneous catalytic decomposition reaction and distillation vessel comprises a decomposition reaction and distillation vessel having 3~5 decomposition reaction chambers; a tubular heater bundle with steam serving as a heating medium is provided in the decomposition reaction and distillation vessel; a dehydration and rectification column is connected to the decomposition reaction and distillation vessel; the step of performing the homogenous catalytic decomposition of the CHHP comprises steps of:

heating decomposition reaction liquid by the tubular heater bundle to evaporate the cyclohexane in the decomposition liquid;

controlling a flow of the steam as the heating medium to evaporate 20~40 wt % of the cyclohexane in the decomposition liquid in the decomposition reaction and distillation vessel;

entering, by the evaporated cyclohexane, the dehydration and rectification column to be further dehydrated and purified, and then entering, by the evaporated cyclohexane, a condenser at a top of the dehydration and rectification column to be cooled;

next, refluxing a part of the cyclohexane in a liquid phase at a reflux ratio of 0.3~0.5, and returning the rest cyclohexane to an oxidation reactor after rinsing with water, wherein a content of cyclohexanol and cyclohexanone in the part of the cyclohexane is lower than 0.04% by controlling the reflux;

to a first chamber of the decomposition reaction and distillation vessel continuously adding an oil-soluble transitional metal catalyst whose amount is determined to ensure that a content of transitional metal ions in cyclohexane oxidation liquid is 12±10 ppm; and to a second chamber of the decomposition reaction and distillation vessel continuously adding oil-soluble 1-hydroxy ethidene-1,1-diphosphonic acid (di)octyl ester which serves as a scale inhibitor, wherein a weight ratio of the added scale inhibitor and the transitional metal ions of the catalyst is 1:0.8~1.2;

wherein during the step of performing the homogenous catalytic decomposition of the CHHP, a decomposition temperature is controlled at 80° C.~160° C., and a pressure is controlled at 0~1 MPa, wherein the pressure is a gauge pressure.

3. The process, as recited in claim 2, wherein the oil-soluble transitional metal catalyst is one member selected from a group consisting of bis(tert-butyl) chromate, cobalt naphthenate and cobalt octoate; the amount of the added catalyst is determined to ensure that the content of the transitional metal ions in the cyclohexane oxidation liquid is 12±8 ppm.

4. The process, as recited in claim 3, wherein during the step of performing the homogenous catalytic decomposition of the CHHP, the decomposition temperature is controlled at 90±2° C., and the pressure is controlled at 0.03±0.01 MPa, wherein the pressure is the gauge pressure.

5. The process, as recited in claim 2, wherein during the step of performing the homogenous catalytic decomposition of the CHHP, the weight ratio of the added oil-soluble 1-hydroxy ethidene-1,1-diphosphonic acid (di)octyl ester and the transitional metal ions of the catalyst is 1:1.

6. The process, as recited in claim 3, wherein during the step of performing the homogenous catalytic decomposition of the CHHP, the weight ratio of the added oil-soluble 1-hydroxy ethidene-1,1-diphosphonic acid (di)octyl ester and the transitional metal ions of the catalyst is 1:1.

7. The process, as recited in claim 4, wherein during the step of performing the homogenous catalytic decomposition of the CHHP, the weight ratio of the added oil-soluble 1-hydroxy ethidene-1,1-diphosphonic acid (di)octyl ester and the transitional metal ions of the catalyst is 1:1.

8. The process, as recited in claim 2, wherein a reactor residence time of an oxidation mixture liquid containing CHHP in each decomposition reaction chamber of the decomposition reaction and distillation vessel is at a range of 5~8 minutes, totaling 20~40 minutes.

9. The process, as recited in claim 3, wherein a reactor residence time of an oxidation mixture liquid containing CHHP in each decomposition reaction chamber of the decomposition reaction and distillation vessel is at a range of 5~8 minutes, totaling 20~40 minutes.

10. The process, as recited in claim 4, wherein a reactor residence time of an oxidation mixture liquid containing CHHP in each decomposition reaction chamber of the decomposition reaction and distillation vessel is at a range of 5~8 minutes, totaling 20~40 minutes.

11. The process, as recited in claim 1, wherein during the step of performing the homogenous catalytic decomposition of the CHHP, the flow of the steam which serves as the heating medium is controlled to evaporate 30±5% of the cyclohexane in the reaction and distillation vessel.

12. A device of the process for preparing cyclohexanol and cyclohexanone by cyclohexane oxidation as recited in claim 1, comprising the homogeneous catalytic decomposition reaction and distillation vessel which is a decomposition reaction and distillation vessel having 4 decomposition reaction chambers provided therein, wherein each the decomposition reaction chamber has a tubular heater bundle; and a separating board with a through-hole is provided between each two the decomposition reaction chambers;

wherein a bottom of a first decomposition and reaction chamber has an inlet for the cyclohexane oxidation mixture and a feeding inlet for a catalyst; a bottom of a second decomposition and reaction chamber has a feeding inlet for a scale inhibitor; a bottom of a final decomposition and reaction chamber has a discharging opening; a bottom part of a dehydration and rectification column is connected to the decomposition reaction and distillation vessel; and each the tubular heater bundle has an inlet for a heating medium and a discharging outlet for condensing water.

* * * * *